United States Patent [19]
Stephenson et al.

[11] Patent Number: 5,689,540
[45] Date of Patent: Nov. 18, 1997

[54] X-RAY WATER FRACTION METER

[75] Inventors: Kenneth E. Stephenson, Cambridge, England; Arthur J. Becker, Ridgefield, Conn.

[73] Assignee: Schlumberger Technology Corporation, Ridgefield, Conn.

[21] Appl. No.: 730,547

[22] Filed: Oct. 11, 1996

[51] Int. Cl.[6] ................................................ G01N 23/06
[52] U.S. Cl. ........................................ 378/53; 378/51
[58] Field of Search ............................ 378/53, 51, 52, 378/57, 59, 60, 147, 149

[56] References Cited

U.S. PATENT DOCUMENTS

| | | | |
|---|---|---|---|
| 3,100,261 | 8/1963 | Bigelow | 378/53 X |
| 3,435,220 | 3/1969 | Hanken | 378/53 |
| 4,168,431 | 9/1979 | Henriksen | 378/53 |
| 4,683,759 | 8/1987 | Skarsvaag et al. | 73/861.04 |

FOREIGN PATENT DOCUMENTS

WO93/24811  12/1993  WIPO.

OTHER PUBLICATIONS

Santen et al., *Photon Energy Selection for Dual Energy γ- and/or X-ray Absorption Composition Measurements in Oil-Water-Gas Mixtures*, Nuclear Geophysics, vol. 9, No. 3 (1995) pp. 193–202.

Abouelwafa et al., *The Measurement of Component ratios in Multiphase Systems Using γ-ray attenuation*, J. Phys. E. Sci. Instrum., vol. 13 (1980) pp. 341–345.

Roach et al., *Multiphase Flowmeter for Oil, Water and Gas in Pipelines Based on Gamma-ray Transmission Techniques*, Nucl. Geophys., vol. 8, No. 3 (1994) pp. 225–242.

Rebgetz et al., *Determination of the Volume Fractions of Oil, Water, and Gas by Dual Energy Gamma-ray Transmission*, Nucl. Geophys., vol. 5, No. 4 (1991) pp. 479–490.

*Primary Examiner*—David P. Porta
*Attorney, Agent, or Firm*—Bridgitte L. Jeffery; Keith G. W. Smith

[57] ABSTRACT

An x-ray generator provides a continuous bremsstrahlung photon spectrum for determining the water to liquid ratio in a mixture of oil/water/gas flowing through a pipe located a distance from the generator. A plurality of detectors measure photons passing along a beam path from the generator through the fluid. A detector is also provided to monitor the energy distribution of the generator. A time interval for measuring the output of each detector is established such that small changes in the gas to liquid ratio occur during this interval. An energy bin width is selected to provide a linear approximation of the water to liquid ratio. After binning the counts for each detector, a multi-phase flow characteristic such as the water to liquid fraction, liquid density, or liquid fraction along the beam path is determined.

11 Claims, 2 Drawing Sheets

X-RAY WATER FRACTION METER

BACKGROUND OF THE INVENTION

The present invention relates generally to a tool for measuring properties of materials flowing in a pipe, and more particularly, to an apparatus and method for determining fluid composition using a source which provides a continuous photon spectrum.

Gamma and x-ray attenuation techniques have been proposed and used previously to measure properties of fluids in pipes. One technique teaches the use of two radioisotopes which emit radiation (photons) of different energies to measure multiphase flow rates (Watt, J. S. and Zastawny, H. W., Method and Apparatus for the Measurement of the Mass Flowrates of Fluid Components in a Multiphase Slug Flow, Dec. 9, 1993, WO-9324811). The emission energies of the two radioisotopes are selected such that attenuation of the high energy photons occurs primarily from Compton scattering, while attenuation of the lower energy photons occurs primarily from photoelectric absorption. Since water, oil and gas have different Compton scattering and photoelectric absorption rates, and scattering and absorption in gas can be calibrated or calculated, two radioisotope emissions at different energies can be used to determine the relative fractions of water, oil and gas along the attenuation path. This dual energy technique, however, provides imprecise and inaccurate measurements due to the discrete emission energy of each radioisotopic source. Further, the energies for optimal precision and accuracy vary with diameter of the flow pipe and the relative amounts of gas, oil and water, as has been discussed by Santen, et. al., Nuclear Geophysics, Vol. 9, No. 3 pp. 193–202, 1995. Gamma ray devices having multiple discrete emission energies provide an inaccurate determination of fluid composition as may be seen with reference to Abouelwafa, M. S. A. and Kendall, E. M., J. Phys. E. Sci. Instrum. 13, 341–345 (1980), Roach, G. J., Watt, J. S., Zastawny, H. W., Hartley, P. E., and Ellis, W. K., Nuclear Geophysics 8, 225–242 (1994), and Rebgetz, M. D., Watt, J. S., and Zastawny, H. W., Nuclear Geophysics 5, 479–490 (1991).

SUMMARY OF THE INVENTION

The above disadvantages of the prior art are overcome by means of the subject invention. An apparatus for measuring water to liquid ratio in a multi-phase flow comprises an x-ray generator providing a continuous photon spectrum and a flow pipe located a distance from the x-ray generator. A plurality of detectors measure photons passing from the generator through the fluid. A detector is also provided to monitor the energy distribution of the generator.

A method for determining a multi-phase flow characteristic comprises the steps of providing a continuous photon spectrum through a fluid filled pipe and a plurality of detectors for measuring the photons and defining a beam path through the pipe to at least one detector. The attenuation of oil, water, and gas is calibrated and the count rates for each detector are normalized against the output of a detector which monitors the energy distribution of the x-ray generator. A time interval is established for measuring the output of each detector such that small changes in the gas to liquid ratio occur during this interval and an energy bin width is selected to provide a linear approximation of the water to liquid atio. After binning the detector counts, the water to liquid fraction, liquid density, or liquid fraction along the beam path are determined.

BRIEF DESCRIPTION OF THE DRAWINGS

The advantages of the present invention will become apparent from the following description of the accompanying drawings. It is to be understood that the drawings are to be used for the purpose of illustration only, and not as a definition of the invention.

In the drawings.

DETAILED DESCRIPTION OF THE PREFERRED EMBODIMENT

Figure 1:
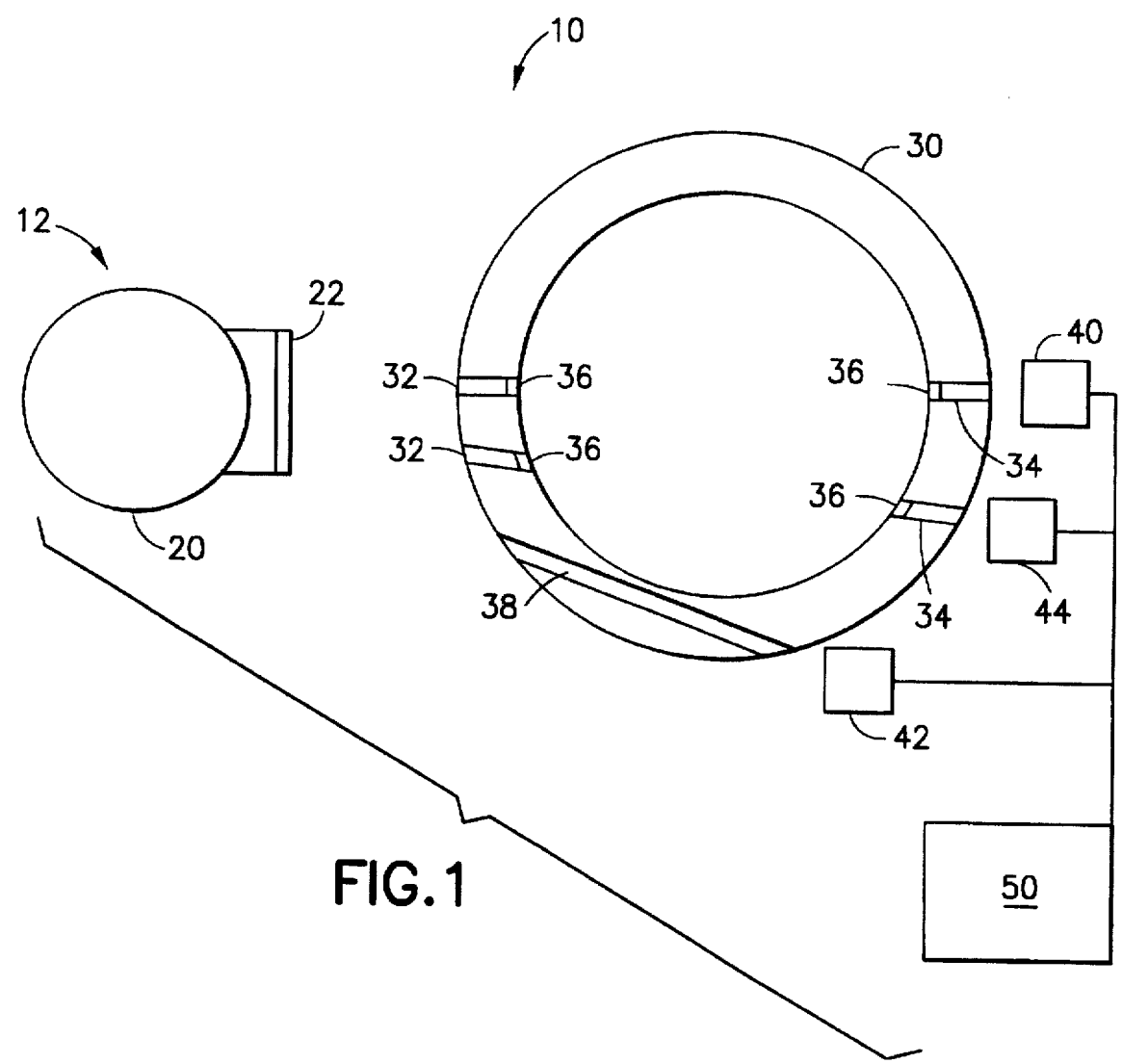
FIG. 1 is a sectional view of the apparatus.

FIG. 1 illustrates an apparatus 10 according to the invention. The apparatus 10 comprises a source 12 and a flow pipe 14 oriented vertically or horizontally oriented. In a preferred embodiment, the apparatus 10 is located uphole, however, it is well within contemplation of the invention for the apparatus 10 to be located downhole.

The source 12 is preferably an x-ray generator 20 providing a continuous bremsstrahlung spectrum ranging from 20–150 keV. The X-ray generator 20 has a target onto which accelerated electrons impinge so as to produce x-rays, the target being held at substantially ground potential. Such a source is described in co-pending application Ser. No. 08/630,736 (Attorney Docket No. 60.1222) which is incorporated herein by this reference. A conventional x-ray generator is within contemplation of the invention so long as the beam current, accelerating voltage, and beam spot position are stable in time. The X-ray generator 20 has an exit window 22 to prevent absorption of low energy x-ray photons. Window 22 is preferably a low density, low-Z window comprised of beryllium, boron carbide, epoxy, or a similar material.

A generally cylindrical pipe 30 is located a distance from the source 12. The distance is determined by the pipe diameter and the angles of the energy beams exiting window 22. The pipe 30 has a plurality of source collimators 32 and a plurality of detector collimators 34 which extend from the outer diameter of the pipe through the pipe wall. The collimators 32 and 34 are comprised of a high-Z material, such as tungsten or a similar material. The diameter of collimator 32 establishes a beam width which is substantially less than an energy beam path distance through the fluid. Preferably, the beam width is less than the diameter of gas bubbles in the fluid. Windows 36 are provided at one end of each collimator 32 and 34 to allow transmission of X-rays through the pipe to a plurality of x-ray detectors 40, 42, 44 while keeping the fluid contained within the pipe 30. The detectors 40, 42, 44 are preferably high speed solid state detectors such as a cadmium zinc telluride detector, however, a scintillator detector, such as NaI(T1), is also within contemplation of this invention. The detector electronics (not shown) bin the detected energy into histograms as a function of energy.

A first beam path passes diametrically through the pipe and detector collimator 34 to a first detector 40. A second beam path passes through a channel 38 in the pipe wall to a second detector 42 which constantly monitors the intensity and energy distribution of the x-ray flux without any influence due to the fluid flowing in the pipe. With a high gas flow in the pipe 30, as a result of the slip velocity between gas and liquids present in the pipe, the gas will generally occupy the region in the center of the pipe and the liquid will occupy the region along the pipe wall 31. In an alternative embodiment, a third beam path passes through a liquid-rich region of the pipe, such as near the pipe wall, to a third detector 44. The accuracy in determining the water to liquid ratio increases when the energy beam passes primarily through liquid rather than gas. Various means for enhancing the liquid fraction along a beam path are within contemplation of this invention. A cross section of the pipe may have a non-cylindrical shape, such as a "D" shape, wherein the collimator 32 directs the energy beam along the straight line portion of the cross section. Alternatively, a beam may be directed through the liquid rich region along a side of the generally cylindrical pipe immediately adjacent to a substantially L-shaped bend in the pipe.

Figure 2:
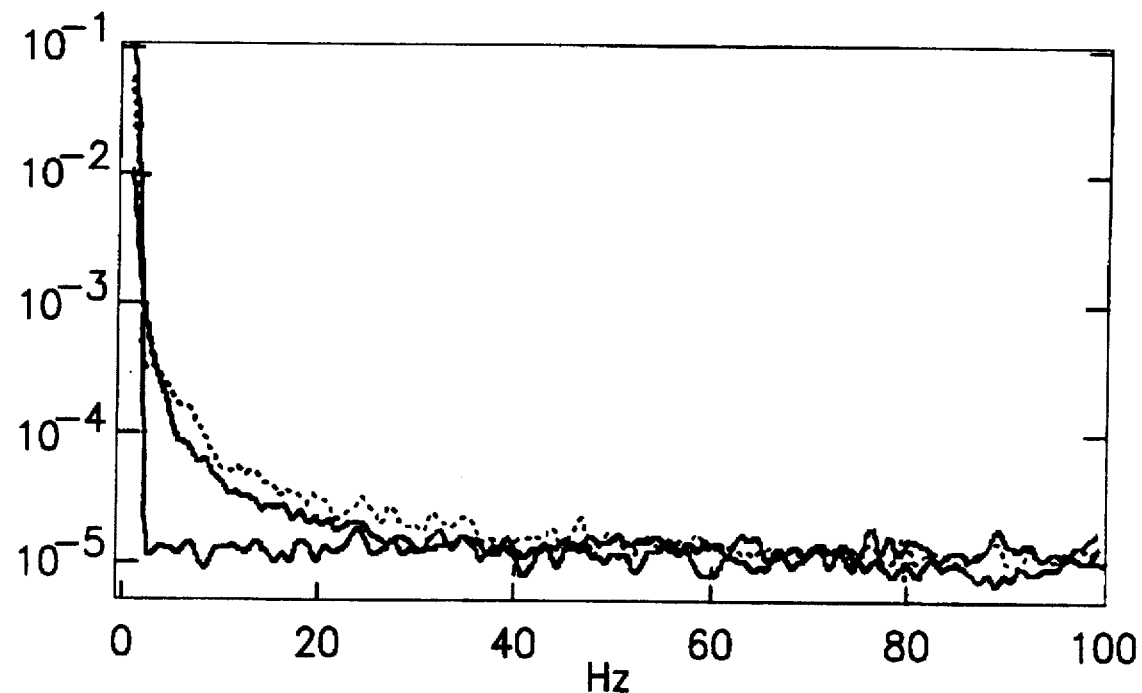
FIG. 2 shows a power spectra of the counts in a high energy bin.
Figure 3:
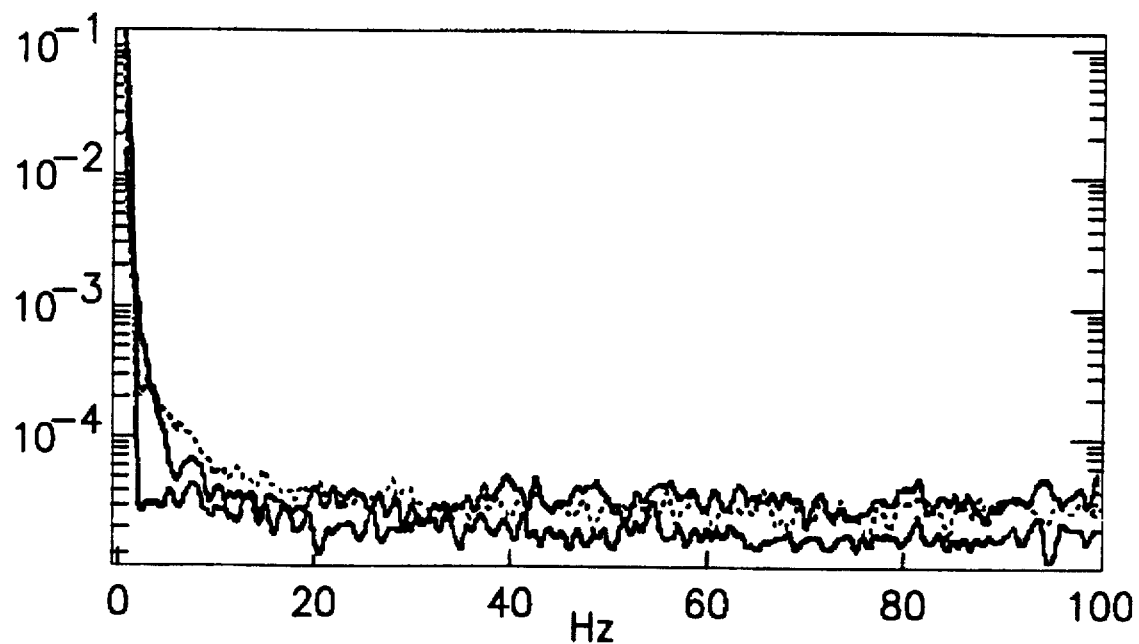
FIG. 3 shows a power spectra of the counts in a low energy bin.

A data acquisition system 50 is connected to the plurality of detectors 40, 42, and 44. The system 50 is capable of binning detected energies into histograms as a function of energy levels. The count binning time interval must be sufficiently short so that only very small changes in the gas to liquid ratio occur during each interval. Power spectra of the counts for the first detector 40 in a high and low energy bin are shown in FIG. 2 and FIG. 3, respectively. The data indicates a suitable timing interval having a resolution of approximately 20 Hz. An energy binning width is selected to provide a linear approximation of the water to liquid ratio. In a preferred embodiment, the binning width is no greater than 6 keV.

In the subject invention, when a pipe 30 contains an unknown mixture of oil, water, and gas, the first beam path, which traverses the diameter of the pipe, will travel a fraction $\alpha_o$ of the diameter in oil, a fraction $\alpha_w$ of the diameter in water, and a fraction $\alpha_g$ of the diameter in gas. In traversing the pipe, photons are lost from the beam through photoelectric absorption and Compton scattering. Such an attenuation process is described by an exponential decay law:

$$N(E_H) = N_v(E_H) exp[-\mu_w(E_H)\alpha_w d - \mu_o(E_H)\alpha_o d - \mu_g(E_H)\alpha_g d]$$

where $N(E_H)$ is the normalized count total, $N_v$ is the normalized count total for an evacuated pipe, $\alpha_w$, $\alpha_o$, and $\alpha_g$ are the respective fractions of water, oil and gas along the attenuation path, d is the diameter of the flow pipe, and $\mu_w$, $\mu_o$, $\mu_g$ are the linear attenuation coefficients for water, oil and gas, respectively, at the binning energy $E_H$. For a lower energy bin $E_L$, a similar relationship holds:

$$N(E_L) = N_v(E_L) exp[-\mu_w(E_L)\alpha_w d - \mu_o(E_L)\alpha_o d - \mu_g(E_L)\alpha_g d]$$

If the constituents of the fluid were known exactly, the attenuation coefficients could be calculated from known cross sections. In practice, however, the produced water has dissolved salts of unknown concentration, and the oil contains sulfur; these affect the attenuation significantly. The solution is to calibrate the attenuation coefficients through attenuation measurements on samples of produced gas, water and oil. The normalized count totals normalized to the constant x-ray generator output flux determined by the monitor detector are:

$$N_g(E) = N_v(E) exp[-\mu_g(E)d]$$

$$N_w(E) = N_v(E) exp[-\mu_w(E)d]$$

$$N_o(E) = N_v(E) exp[-\mu_o(E)d]$$

Calibration constants for a high energy bin are defined as follows:

$$x_w \equiv \ln\left[\frac{N_w(E_H)}{N_g(E_H)}\right] = -\mu_w(E_H)d + \mu_g(E_H)d$$

$$x_o \equiv -\mu_o(E_H)d + \mu_g(E_H)d$$

and for a low energy bin:

$$y_w \equiv \ln\left[\frac{N_w(E_L)}{N_g(E_L)}\right] = -\mu_w(E_L)d + \mu_g(E_L)d$$

$$y_o \equiv -\mu_o(E_L)d + \mu_g(E_L)d$$

For any given normalized count total, $N_s$, for an unknown flow, similar quantities can be defined in terms of the calibration constants:

$$x_s \equiv \ln\left[\frac{N_s(E_H)}{N_g(E_H)}\right] = \alpha_w x_w + \alpha_o x_o \quad (1)$$

$$y_s \equiv \ln\left[\frac{N_s(E_L)}{N_g(E_L)}\right] = \alpha_w y_w + \alpha_o y_o \quad (2)$$

Equations 1-2 represent a system of equations which can be solved for unknowns $\alpha_w$, and $\alpha_o$. The values derived, however, can have poor statistical precision because of the required short integration time. The integration time must be sufficiently short that the values of $\alpha_w$ and $\alpha_o$ do not change significantly over the integration period. The following sums are constructed over repeated measurements:

$$\Sigma x_s = x_w \Sigma \alpha_w + x_o \Sigma \alpha_o \quad (3)$$

$$\Sigma y_s = y_w \Sigma \alpha_w + y_o \Sigma \alpha_o \quad (4)$$

$$\Sigma \alpha_o = \frac{y_w \Sigma x_s - x_w \Sigma y_s}{x_o y_w - x_w y_o} \quad (5)$$

$$\Sigma \alpha_w = \frac{y_o \Sigma x_s - x_o \Sigma y_s}{x_w y_o - x_o y_w} \quad (6)$$

$$\Sigma \alpha_l = \Sigma(\alpha_w + \alpha_o) = \Sigma \alpha_w + \Sigma \alpha_o \quad (7)$$

The desired result is the average water to liquid volume fraction weighted by the fraction of liquid in the pipe determined by the following relationship:

$$\overline{\left(\frac{\alpha_w}{\alpha_l}\right)} = \frac{\Sigma\left(\frac{\alpha_w}{\alpha_l}\right)\alpha_l}{\Sigma \alpha_l} = \frac{\Sigma \alpha_w}{\Sigma \alpha_l} \quad (8)$$

In addition, the average liquid fraction along the beam path, $\alpha_l$, is obtained from Equation 7. When the densities of pure oil and water, $\rho_o$ and $\rho_w$ are known from other measurements, the average liquid density may be calculated:

$$\rho_l = \frac{\Sigma \alpha_w \rho_w + \Sigma \alpha_o \rho_o}{\Sigma \alpha_l} \quad (9)$$

The foregoing description of the preferred and alternate embodiments of the present invention have been presented for purposes of illustration and description. It is not intended to be exhaustive or limit the invention to the precise form disclosed. Obviously, many modifications and variations will be apparent to those skilled in the art. The embodiments were chosen and described in order to best explain the principles of the invention and its practical application thereby enabling others skilled in the art to understand the invention for various embodiments and with various modifications as are suited to the particular use contemplated. It is intended that the scope of the invention be defined by the accompanying claims and their equivalents.

What I claim is:

1. An apparatus for measuring water to liquid ratio in a multi-phase flow, comprising:

means for providing a continuous bremsstrahlung photon spectrum;

a pipe located a distance from the photon spectrum means, the pipe containing a fluid mixture of oil, water, and gas;

a plurality of detectors for measuring photons passing from the photon spectrum means through the fluid; and, means for monitoring an energy distribution of the photon spectrum means.

2. The apparatus of claim 1, wherein the pipe further comprises a plurality of collimators which extend from the outer diameter of the pipe through the pipe wall, each collimator having a means for retaining the fluid within the pipe.

3. The apparatus of claim 2 wherein the photon spectrum means comprises an x-ray generator and the retaining means are comprised of a low-Z material to prevent severe attenuation of x-rays.

4. The apparatus of claim 3 further comprising electronic means for counting the detected photons as a function of energy levels.

5. The apparatus of claim 4, wherein the pipe has a generally cylindrical wall and a beam path passes diametrically through the pipe to at least one of the detectors.

6. The apparatus of claim 4, wherein the pipe wall has a substantially linear section and a beam path passes through a liquid-rich zone adjacent to the linear section.

7. The apparatus of claim 1, wherein the monitoring means lies along a beam path which passes only through the pipe wall.

8. A method for determining a multi-phase flow characteristic, comprising the steps of:

a) providing a continuous photon spectrum through a fluid filled pipe and a plurality of detectors for measuring the photons;

b) defining a beam path through the pipe to at least one detector;

c) calibrating the attenuation of oil, water, and gas;

d) normalizing the count rates for each detector;

e) establishing a time interval for measuring the output of each detector such that small changes in the gas to liquid ratio occur during this interval;

f) selecting an energy bin width to provide a linear approximation of the water to liquid ratio;

g) binning the detector counts; and h) determining the water to liquid fraction, liquid density, or liquid fraction along the beam path.

9. The method of claim 8, wherein the energy bin width is approximately 6 keV.

10. The method of claim 8, wherein the time interval is approximately 50 ms.

11. The method of claim 8, further comprising:

extracting detector counts that indicate a high density before performing step (h).

\* \* \* \* \*